United States Patent

Schouwenburg

[11] Patent Number: 5,935,165
[45] Date of Patent: Aug. 10, 1999

[54] VOICE PROSTHESIS, AND CONTROL UNIT FOR USE IN THE FITTING THEREOF

[76] Inventor: Paul Ferdinand Schouwenburg, Grenslaan 4, NL-2111 GH Aerdenhout, Netherlands

[21] Appl. No.: 08/930,101

[22] PCT Filed: May 8, 1996

[86] PCT No.: PCT/NL96/00199

§ 371 Date: Nov. 10, 1997

§ 102(e) Date: Nov. 10, 1997

[87] PCT Pub. No.: WO96/35399

PCT Pub. Date: Nov. 14, 1996

[30] Foreign Application Priority Data

May 12, 1995 [NL] Netherlands .......................... 1000355

[51] Int. Cl.⁶ .............................. A61F 2/20; A61F 2/04
[52] U.S. Cl. ........................ 623/9; 128/207.16; 606/196
[58] Field of Search .................................. 623/9–12, 66; 128/207.16; 606/196

[56] References Cited

U.S. PATENT DOCUMENTS

| | | |
|---|---|---|
| 3,447,533 | 6/1969 | Spicer . |
| 4,435,853 | 3/1984 | Blom et al. .................... 623/9 |
| 4,610,691 | 9/1986 | Depel et al. ................... 623/9 |
| 4,820,304 | 4/1989 | Depel et al. ................... 623/9 |
| 4,911,716 | 3/1990 | Blom et al. .................... 623/9 |
| 5,064,433 | 11/1991 | Blom et al. .................... 623/9 |
| 5,306,298 | 4/1994 | Godley, III et al. ........... 623/9 |
| 5,314,470 | 5/1994 | Persson ........................ 623/9 |
| 5,391,205 | 2/1995 | Knight ......................... 623/9 |
| 5,433,747 | 7/1995 | Grundei ........................ 623/9 |
| 5,480,432 | 1/1996 | Suding et al. ................. 623/9 |
| 5,507,809 | 4/1996 | Blom ............................ 623/9 |
| 5,571,180 | 11/1996 | Blom ............................ 623/9 |
| 5,578,083 | 11/1996 | Laguette et al. .............. 623/9 |
| 5,738,095 | 4/1998 | Persson ..................... 128/207.14 |

FOREIGN PATENT DOCUMENTS 551198  7/1993  European Pat. Off. .
2077109  12/1981  United Kingdom .

*Primary Examiner*—David J. Isabella
*Assistant Examiner*—Choon P. Koh
*Attorney, Agent, or Firm*—Sughrue, Mion, Zinn, Macpeak & Seas, PLLC

[57] ABSTRACT

A voice prosthesis intended for placing in an opening in the wall between the oesophagus and the windpipe, in the case of which the windpipe opens out into the neck by way of a stoma, comprises a tubular element which at one end has an external enlargement, and at the other end has retaining means which are expandable outwards from a contracted position to a spread position, which prosthesis with the retaining means in the contracted position can be fitted by way of the windpipe stoma in such a way that the tubular element goes into the opening and the external enlargement comes to rest against the wall part of the windpipe around said opening, and the retaining means can be fitted against the wall part of the oesophagus around said opening after the tubular element has been placed in said opening. The retaining means comprise one or more projections which can be moved between a contracted position essentially in line with the tubular element and a spread position, in such a way that each projection can be gripped by a control unit which can be placed in said cavity, in order to move each projection between the above-mentioned positions. These control elements bear a ball-type valve in an elastic manner.

20 Claims, 4 Drawing Sheets

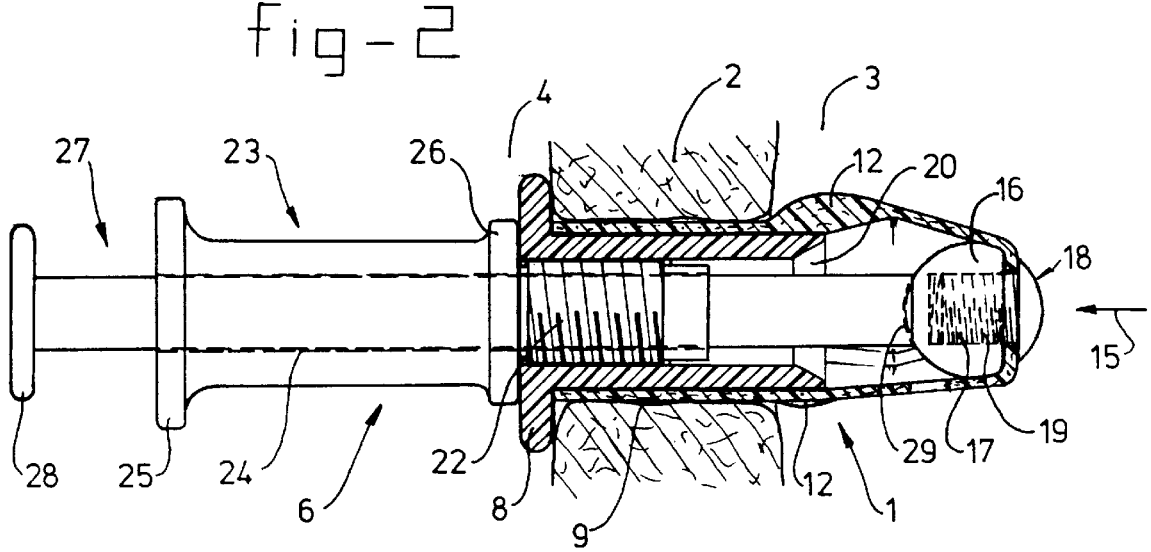
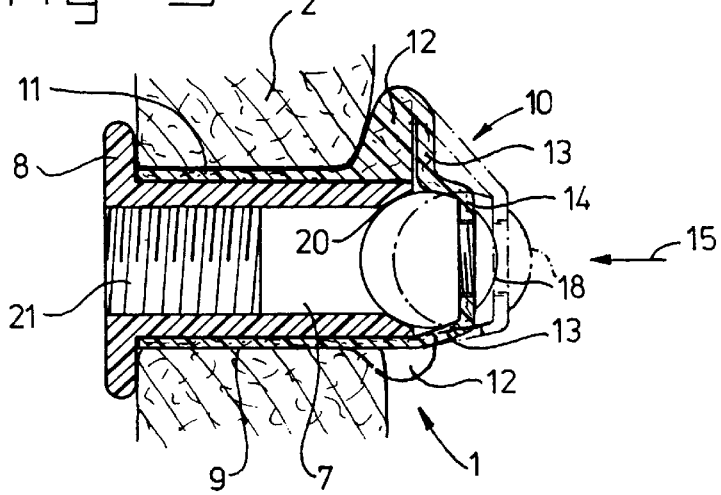
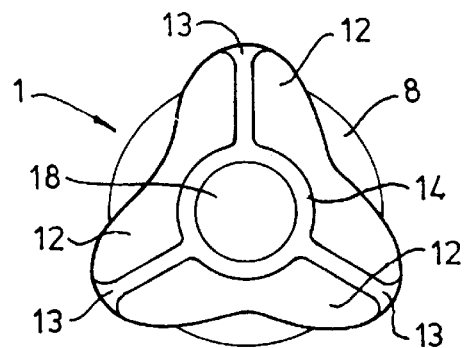

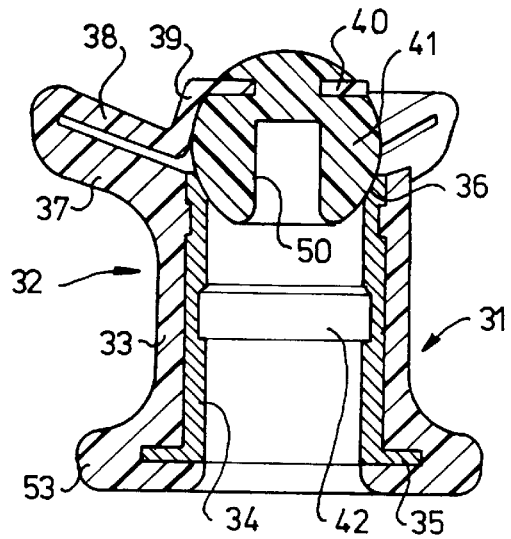
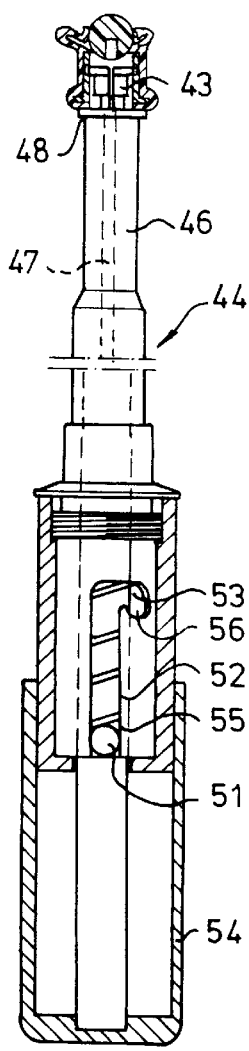
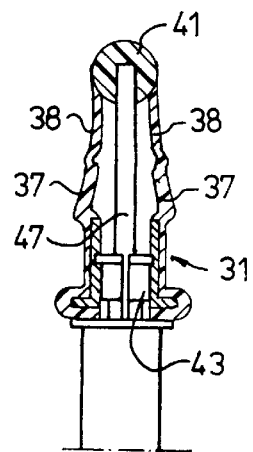

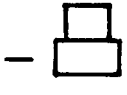
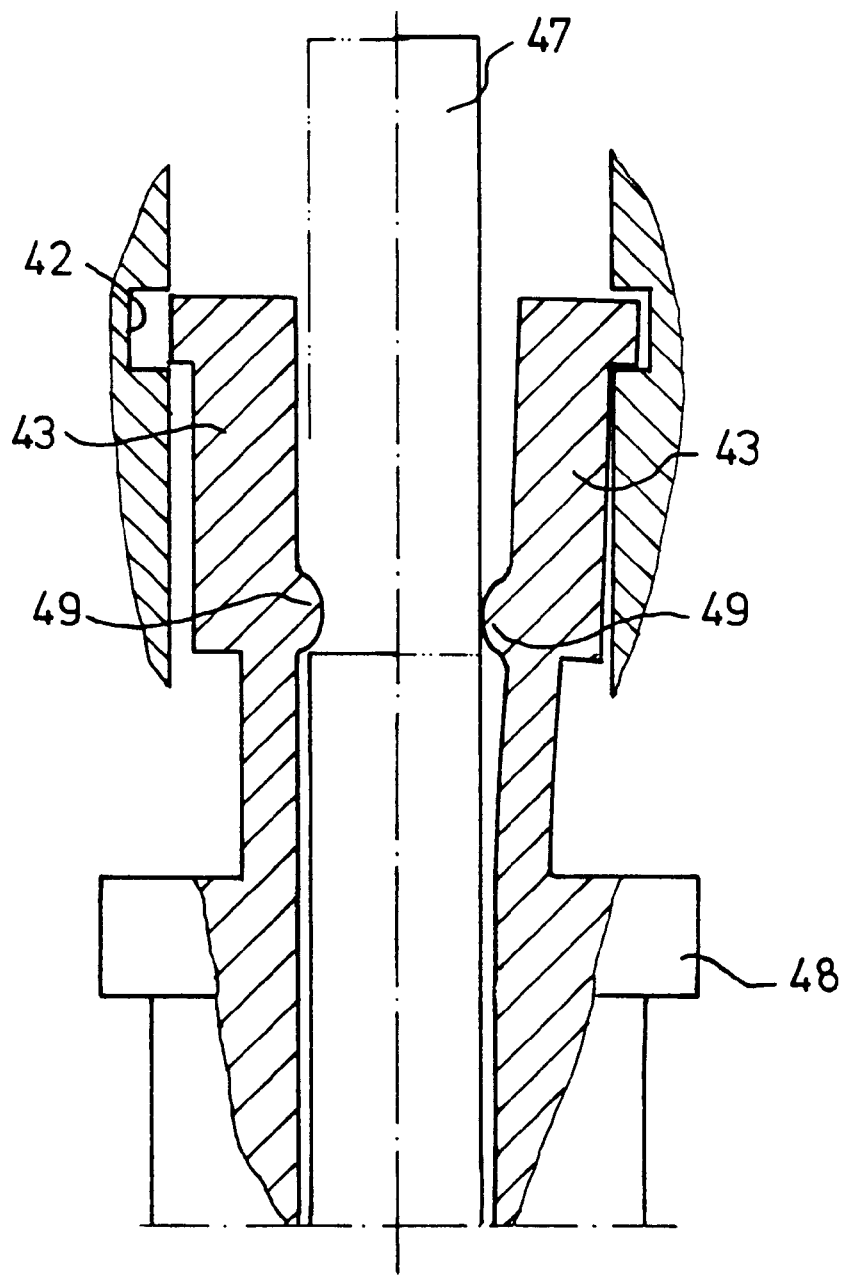

VOICE PROSTHESIS, AND CONTROL UNIT FOR USE IN THE FITTING THEREOF

The invention relates to a voice prosthesis for patients whose larynx has been removed. The voice prosthesis is intended for placing in an opening in the wall between the oesophagus and the windpipe, in which case the windpipe opens out into the neck by way of a stoma, which prosthesis comprises a tubular element which is provided with an internal, throughgoing cavity and at one end has an external enlargement, and at the other end has retaining means which are movable between a contracted position and a spread position, which prosthesis with the retaining means in the contracted position can be fitted by way of the windpipe stoma in such a way that the tubular element goes into the opening and the external enlargement comes to rest against the wall part of the windpipe around said opening, and the retaining means can be fitted against the wall part of the oesophagus around said opening after the tubular element has been placed in said opening.

Such a voice prosthesis is known from U.S. Pat. No. 5,300,119. This known voice prosthesis has a tubular element which has at both ends an external, circular flange. For the purpose of placing the voice prosthesis, the flange which has to go into the oesophagus is held in the contracted state by means of a cap placed thereon. Said cap, which consists of a gelatine, dissolves shortly after the voice prosthesis has been placed in position, under the influence of the environment prevailing in the oesophagus, and the flange expands to the spread position as a result of its initial tension. The fixing of this voice prosthesis is now complete.

This known voice prosthesis has various disadvantages. For example, the initial tension of the contracted flange must not be too great, otherwise the gelatine cap would give way too soon. Moreover, tissue damage must not occur during removal. The result of this is that the retaining action of the flange in its spread position is limited, which means that there is a risk of the voice prosthesis becoming dislodged and going into the windpipe.

In order to limit that risk, the prosthesis is sometimes fixed additionally with adhesive strip or adhesive plaster. Such an additional fixing is not so desirable, since it is visible and is consequently tiresome for the user, and it involves an additional action.

Another disadvantage is that basically the voice prosthesis can be used and checked reliably only by a specialist (ENT specialist), especially since the fitting of this voice prosthesis is found to be a difficult operation and cannot be checked definitively without an x-ray. Besides, due to the materials used, the prosthesis is susceptible to fungal infections.

The object of the invention is therefore to provide a voice prosthesis which does not have these disadvantages. That object is achieved through the fact that the retaining means comprise at least one projection which can be gripped by a control unit, operating through said cavity, for moving each projection between the abovementioned positions.

In the case of the voice prosthesis according to the invention each projection, by means of which it must ultimately be retained, is held in the contracted position by means of a separate control unit. Such a control unit makes it possible to exert a reasonably great force on the projections. As a result of this, the initial tension by means of which the projections are forced to their spread position, and thus the retaining force of the voice prosthesis, can be selected at such a high level that the risk of the voice prosthesis becoming dislodged can be prevented entirely.

The retaining means can have at least two projections, extending radially relative to the tubular element and distributed at regular intervals over the periphery of said tubular element, which projections can move from the retracted position to the spread position under the influence of an initial tension. An embodiment with three projections distributed at regular intervals is preferred.

Good results are obtained in the case of an embodiment in which each projection is provided with a control element, which control elements are each connected to the outermost end of the corresponding projection and in the spread position thereof extend essentially parallel thereto towards and at least partially over the cavity of the tubular element. In the last region the control elements can interact with a control unit in the form of, for example, a pin.

The voice prosthesis can be in one piece if the connections between projections and the tubular element and the connections between each projection and a control element are made elastic.

According to a preferred embodiment, the control elements can bear a valve body at their ends facing each other, and the end of the tubular element facing that can be in the form of a valve seat, in such a way that in the spread position of the projections the valve body can interact with the valve seat.

The valve body is suspended from, for example, three projections with corresponding control elements. In the case of such a suspension the valve body can make movements parallel to itself towards and away from the valve seat. Unlike the situation where there is a pivoting movement, even with the slightest movement of the valve body away from the seat a gap of uniform dimensions is formed over the entire periphery, and this improves the effect of the valve body both in letting through air and in shutting off.

Such a valve body can reliably prevent substances from the oesophagus from going into the windpipe. The valve body suspended in this way, when open, also provides a relatively large passage, since a broad throughflow area is formed along the entire periphery thereof, with the exception of the areas where the control elements are situated.

In particular, in this case the part of the control elements and/or the valve body extending over the cavity of the tubular element can form a stop face against which the control unit can be placed, in such a way that, through relative movement of said control unit with respect to the tubular element, the projections and/or the valve body can be moved away from the tubular element, taking the projections along with them to their contracted position.

The connections between the control elements and the valve body can also be made elastic. Furthermore, the valve body can rest under initial tension against the valve seat, in order to achieve the desired seal.

In the spread position, each projection preferably forms an acute angle with the lengthwise direction of the tubular element, in such a way that in the spread position each projection and corresponding control element faces obliquely away from the tubular element. In this embodiment any bending or shifting movements of the projections which may occur, for example as a result of muscle movements or swallowing movements, have no effect on the position of the valve body against the seat.

In that connection good results are obtained with an embodiment in which at its end facing the valve body each control element has a leg which is bent at an essentially right angle away from the tubular element and to which the valve body is connected, and in the spread position each leg is under initial tension in the direction of the valve body.

The invention also relates to a set, comprising a voice prosthesis according to one of the preceding claims, and also a control unit which can be placed in the cavity of the tubular element, which control unit has a stop face which can be made to interact with the projections and/or the valve body. By placing the stop face of the control unit against valve body or projections, these elements can be pushed away from the tubular element in such a way that they reach their contracted position. This produces pulling forces in the voice prosthesis, and in order to ensure that this does not make the valve body shift relative to the stop face, the control unit can have a pin which can be slid in the lengthwise direction and can be centered in a corresponding recess in the valve body.

The control unit can also have a stop which can be made to interact with the tubular element. Said stop can be in the form of an internal recess in the tubular element, in which an expansion means of the control unit can be accommodated. In order to ensure ease of use, the expansion means can be expandable by sliding the projection in the lengthwise direction.

In a practical embodiment, the control unit comprises a hollow rod, having at one end at least two barbed spreading fingers facing away from each other, and a pin which is slidable in the hollow rod, which spreading fingers and pin interact with each other at their surfaces facing each other, in such a way that when the pin is slid through the hollow rod the spreading fingers expand and the pin reaches a projecting position where it comes out of the end of the hollow rod.

Of course, the control unit discussed above is used both for fitting and for removing the voice prosthesis. Removal using the control unit has the advantage that injuries as the result of mechanical damage are avoided.

Another great advantage of the voice prosthesis is that it is simple to check whether it is in the correct position by exerting a certain pulling force. It is not necessary to make x-rays for this.

The invention will be explained in greater detail below with reference to an exemplary embodiment shown in the figures.

FIG. 2 shows the voice prosthesis, in section, and a control unit during fitting of the voice prosthesis.

FIG. 3 shows a view, in section, of the fitted voice prosthesis.

FIG. 4 shows a view of the voice prosthesis according to FIG. 3.

FIG. 5 shows a second embodiment of the voice prosthesis, in section.

FIG. 6 shows the voice prosthesis according to FIG. 5, fitted on a control unit.

FIG. 7 shows a voice prosthesis according to FIGS. 5 and 6, with a part of the control unit, and with the prosthesis in the contracted position.

FIG. 8 shows a detail of insertion unit and voice prosthesis in section.

Figure 1:
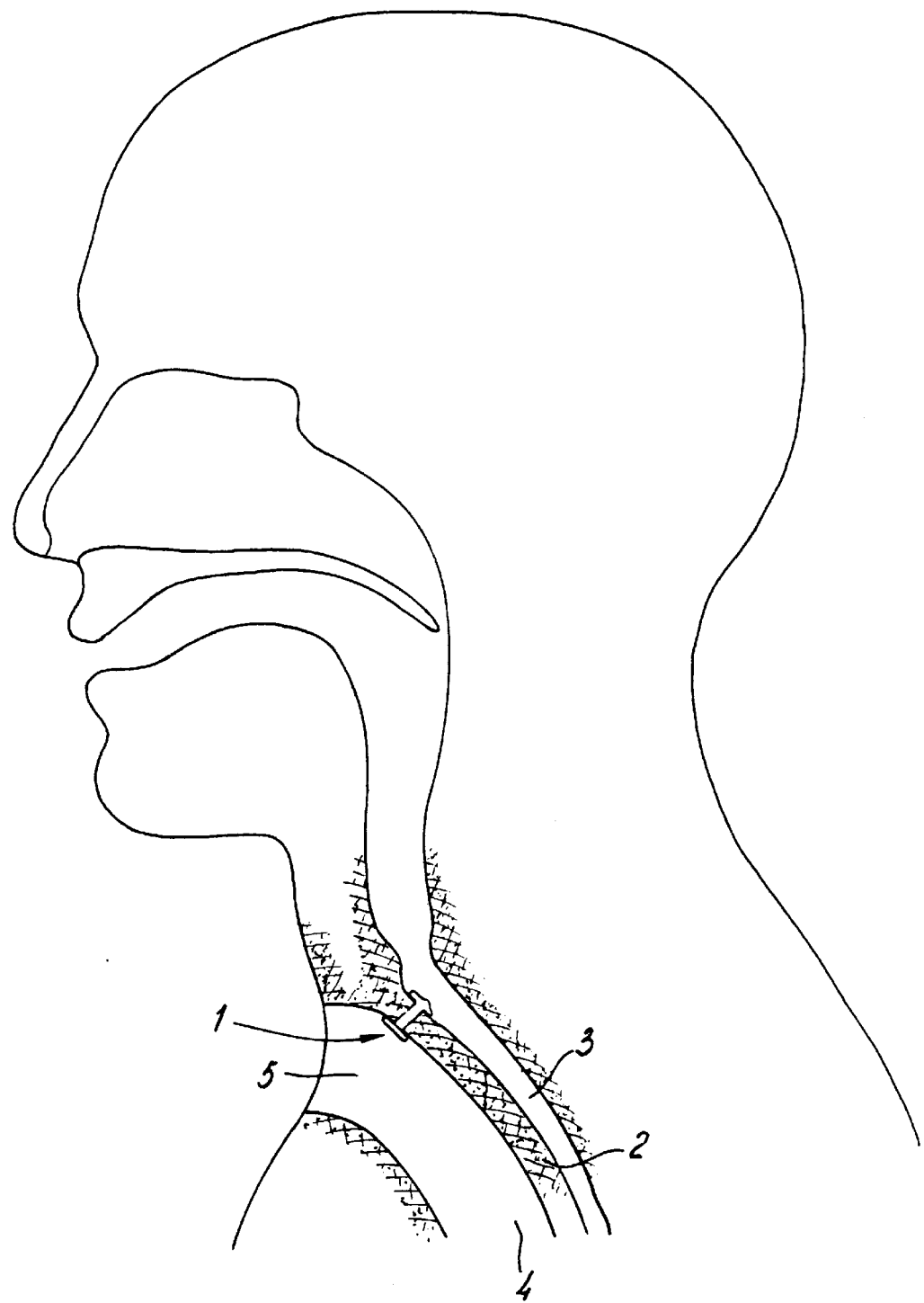
FIG. 1 shows the voice prosthesis according to the invention fitted in a patient.

As shown in FIG. 1, a voice prosthesis, which is indicated in its entirety by 1, is fitted in the patient 2 in the wall between oesophagus 3 and windpipe 4. Said windpipe 4 opens by way of stoma 5 into the patient's neck.

FIG. 2 shows the prosthesis 1 in the position in which it is fitted in said wall 2 by means of control unit 6. As can also be seen clearly from FIG. 3, said voice prosthesis 1 has a tubular part 7 with an external flange 8 which rests against the part of the wall of the windpipe 4 around the opening 9 in which the voice prosthesis 1 is fitted. The tubular part 7 and the external flange form a unit of relatively rigid plastic. It is also conceivable to make this part from another material, for example a metal or silicone rubber.

The voice prosthesis 1 also comprises a part made of a relatively flexible plastic, indicated in its entirety by 10. This part 10 also comprises a tubular sleeve 11, which is clamped under initial tension around tubular part 7. Three projections 12 are provided at the end of the sleeve 11 facing away from the external flange 8. These three projections 12 rest against the wall of the oesophagus, around the opening 9, when the voice prosthesis 1 is fitted.

The control elements 13 are made integral with the projections 12. Said control elements 13 are each fixed to a projection 12 at their outer end, and to a ring 14 at their inner end.

The ring 14 in turn has suspended from it a valve body, indicated in its entirety by 15. Said valve body 15 comprises a ball part 16 which is provided with internal screw thread 17. The valve body 15 also has a screw part 18, which has a threaded stem 19. The stem 19 is screwed into the screw thread 17 of ball part 16, in such a way that the ring 14 is clamped between the ball part 16 and the screw part 18.

The ball part 16 and the screw part 18 can be made of plastic, but they can also be of metal. Other materials are also possible.

The valve seat, indicated by 20, is provided at the end of the tubular part 7 facing the valve body 15. Said valve seat 20 is made conical or partially bowl-shaped, in such a way that the valve body 15 can seal reliably relative to said valve seat 20.

The valve body 15 preferably rests under initial tension against the valve seat 20, which can be achieved by a suitable shaping of the flexible part 10, and by a suitable positioning thereof on the tubular part 7.

The procedure for fitting the voice prosthesis 1 according to the invention is as follows. The external screw thread 22 of the control unit 6 is screwed into the part of the tubular part 7 provided with screw thread 21. The external screw thread 22 is situated in particular on the retaining part 23 of said control unit 6, which retaining part 23 also has a gripping surface 24 which is bounded by an outer flange 25 and an inner flange 26.

The retaining part 23 is screwed down firmly with its inner flange 26 against the external flange 8 of the voice prosthesis 1. The retaining part 23 can then be held between two fingers, for example the index finger and the middle finger, while the thumb is placed against the control pin, indicated in its entirety by 27. In particular, the thumb is placed against the gripping surface 28 of the control pin 27. The other end 29 of the control pin rests against the valve body 15. By now pushing the control pin 27 into the retaining part 23, the valve body 15 is pushed off the seat 20, and the control elements 13 force the projections 12 to the position shown in FIG. 2. In this position these projections 12, and also the control elements 13, lie virtually parallel to the axis of the voice prosthesis 1.

In this position the voice prosthesis can easily be pushed into the hole 9. The pressure on the pin 27 is then removed. As a result of the initial tension in the flexible part 10 of the voice prosthesis 1, the projections 12 move to the position shown in FIG. 3. The result of this is twofold.

First of all, the voice prosthesis 1 is now retained reliably in the hole 9. The projections 12 can in fact be of such a rigid type that any chance of the voice prosthesis becoming dislodged from the hole 9 is prevented. Moreover, as a result of the abovementioned initial tension, the valve body 15 comes to rest against the seat 20, with the result that a reliable seal is ensured. On the other hand, the valve body 15 can still be moved off the seat 20 if the patient shuts off the stoma 5, and through a build-up of pressure in his windpipe 4, can ensure that air escapes by way of voice prosthesis 1 into the oesophagus 3.

After the voice prosthesis 1 is placed in the hole 9 in this way, the retaining part 23 is unscrewed from the tubular part 7 of the voice prosthesis 1, following which the fitting operation is complete.

The voice prosthesis 31 shown in FIGS. 5 to 8 comprises a part 32 which is made in one piece of a relatively flexible plastic and comprises, inter alia, a tubular sleeve 33 which is clamped around the metal tubular part 34. The tubular part 34 has at its one end an outward pointing flange 35, while its other end 36 forms a valve seat. In turn, the tubular sleeve 33 has a flange-shaped fixing ring 53 which is hooked around the flange 35 of the tubular part 34. At its other end, the tubular sleeve 33 has three projections 37, which project obliquely outwards, facing away a little from the tubular part 34, when the voice prosthesis is in its normal fitted position.

A flexible control element 38, which merges into a leg 39 bent approximately at a right angle, is attached to each projection 37. These three legs are together attached to a fixing ring 40, in which the ball-shaped valve body 41 is fixed.

The legs 39 rest under initial tension against the valve body 41. The valve body 41 also rests under initial tension against the valve seat 36.

The spring-loaded contact of the legs 39 against the valve body 41 has the advantage that slight bending movements of the projections 37, for example in the case of swallowing movements, have virtually no effect on the contact under initial tension of the valve body 41 against the seat 36. Such slight movements, generally directed outwards, of the projections 37 lead to corresponding bending movements of the control elements 38, which in turn make a bending movement relative to the corresponding leg 39. In this case the spring-loaded pressure of the legs 39 against the valve body 41 changes little if at all, which is seen in the fact that the contact of said valve body 41 against the valve seat 36 remains constant.

As can also be seen in FIG. 5, the tubular part 34 has an internal circular groove 42. In this groove 42, in which the spreading fingers 43 of the control unit indicated in its entirety by 44 can be accommodated. This control unit consists of a hollow rod 46, in which the pin 47 is slidable. Fitted at the end of the hollow rod is a flange 48, against which the flange-type fixing ring 53 of the voice prosthesis 31 can rest. In that position the spreading fingers 43 are precisely at the level of the recess 42 in the tubular part 34. The voice prosthesis 31 is locked relative to the control element 44 by now spreading these fingers 43, in such a way that they engage in the recess 42.

The spreading fingers are spread by sliding the pin 47 through the spreading fingers 43. These spreading fingers have an internal bulge 49 (see FIG. 8), against which the head of the pin 47 comes to rest. When the pin 47 is pushed further outwards, the spreading fingers 43 bend outwards a little, with the result that the voice prosthesis 31 is locked on the control element 44.

Pushing the pin 47 further outwards takes it into the recess 50 in the valve body 41, as shown in FIG. 7. The advantage is that the valve body 41 cannot slip off the point of the pin 47, under the influence of the elastic forces which occur when the valve body 41 is pushed further outwards. Under the influence of the control elements 38, the projections 37 are contracted, with the result that the voice prosthesis 31 can be inserted easily and stably in the opening concerned.

A locking mechanism is provided in the control unit 44, in order to hold the voice prosthesis in the position shown in FIG. 7. Said locking mechanism contains a locking rod 51, fitted on the pin 47 and projecting crosswise, and also a groove 52 in the interior of the hollow rod 46. Said groove 52 opens into a transverse groove 53, in which the transverse rod 51 can be turned as soon as it has been pushed sufficiently far upwards.

The spring 55 presses the pin in that position into the recess 56 of transverse groove 53. A handle 54, which makes the operation of the control unit 44 easier, is provided at the end of the pin 47.

I claim:

1. A voice prosthesis placement system for disposing a voice prosthesis in an opening in the wall between the esophagus and the windpipe, there being a stoma communicating said windpipe out of the neck, said system comprising:

a voice prosthesis and a control unit;

said prosthesis comprising:
   a tubular element having an internal, throughgoing cavity,
   a first end including an external enlargement, and
   a second end including retaining means movable between a contracted position and a spread position;

said prosthesis being adapted to be inserted through said stoma so that said tubular element enters said opening and said external enlargement rests against said wall on the side of said windpipe at an area around said opening;

said retaining means being adapted to be fitted against said wall on the side of said esophagus around said opening after said tubular element has been placed in said opening, wherein said retaining means permits insertion and removal of said prosthesis in said spread position;

said retaining means comprising one or more projections grippable by said control unit when said control unit is operated through said throughgoing cavity to move said retaining means between said contracted and said spread positions.

2. The voice prosthesis placement system according to claim 1, wherein said retaining means comprises two or more of said projections, each extending radially relative to said tubular element, distributed at regular intervals over the periphery of said tubular element, and moveable from said contracted position to said spread position under the influence of an initial tension.

3. The voice prosthesis placement system according to claim 1, further comprising:

one or more control elements, each having a corresponding one of said one or more projections;

said one or more control elements each being connected to an outermost end of said corresponding projection at a respective connection;

in said spread position of said corresponding projection, said one or more control elements each extending to and being at least partially over said throughgoing cavity of said tubular element.

4. The voice prosthesis placement system according to claim 3, further comprising:

said one or more projections each being connected to said tubular element at a respective elastic connection; and said connection between each of said one or more control elements and said corresponding one of said one or more projections being elastic.

5. The voice prosthesis placement system according to claim 4, wherein:

said voice prosthesis further comprises a valve body;

each of said one or more control elements have control element ends, all of said control element ends facing each other and bearing a valve body; and said tubular element has a respective end facing said valve body, and forms a valve seat so that when said one or more projections are in said spread position, said valve body interacts with said valve seat.

6. The voice prosthesis placement system according to claim 5, wherein:

said part of said one or more control elements extending over said throughgoing cavity of said tubular element form a stop for said control unit; and said control unit having a part adapted to be disposed in said tubular element to contact said stop so that, through relative movement of said control unit with respect to said tubular element, said control unit biases said one or more projections away from said tubular element and toward said contracted position.

7. The voice prosthesis placement system according to claim 6, wherein respective connections between said one or more control elements and said valve body are elastic.

8. The voice prosthesis placement system according to claim 5, wherein said valve body rests, under initial tension, against said valve seat.

9. The voice prosthesis placement system according to claim 3, wherein, in said spread position, each of said one or more projections is directed transversely to a lengthwise direction defined by said tubular element.

10. The voice prosthesis placement system according to claim 9, wherein, in said spread position, each of said one or more projections forms an acute angle with a lengthwise direction defined by said tubular element.

11. The voice prosthesis placement system according to claim 10, wherein, in said spread position, each said one or more projections and said corresponding one or more control elements faces obliquely away from said tubular element.

12. The voice prosthesis placement system according to claim 11, wherein, at said respective end of said tubular element facing said valve body, each of said one or more control elements has a respective leg bent at a substantially right angle away from said tubular element, each said respective leg being connected to said valve body.

13. The voice prosthesis placement system according to claim 12, wherein, in said spread position, each said respective leg is under initial tension in the direction of said valve body.

14. The voice prosthesis placement system according to claim 5, wherein said control unit has a stop face adapted to interact with said valve body.

15. The voice prosthesis placement system according to claim 14, wherein said control unit has a pin which is slidable in a lengthwise direction and can be centered in a corresponding recess in said valve body.

16. The voice prosthesis placement system according to claim 15, wherein said control unit has a stop adapted to interact with said tubular element.

17. The voice prosthesis placement system according to claim 16, wherein said control unit has means for expanding said tubular element, and wherein said tubular element has an internal recess adapted to accommodate said expansion means of said control unit.

18. The voice prosthesis placement system according to claim 17, wherein said expansion means expands said tubular element in response to said sliding of said pin in said lengthwise direction.

19. The voice prosthesis placement system according to claim 1, wherein:

said control unit comprises:

a hollow rod having at one end at least two barbed, spreading fingers facing away from each other, and a pin slidable in said hollow rod;

said spreading fingers and said pin interacting at facing surfaces so that, when said pin slides through said hollow rod, said at least two spreading fingers expand and said pin extends from said one end of said hollow rod.

20. The voice prosthesis placement system according to claim 19, further comprising means for locking said pin in said hollow rod in a projecting position so that said pin extends from said one end of said hollow rod.

\* \* \* \* \*